United States Patent [19]

Taylor et al.

[11] Patent Number: 4,927,828
[45] Date of Patent: * May 22, 1990

[54] DIASTEREOISOMERIC TETRAHYDROPYRIDO-(2,3,D) PYRIMIDINE DERIVATIVES

[75] Inventors: Edward C. Taylor, Princeton, N.J.; George P. Beardsley, Essex, Conn.; Chuan Shih, Indianapolis, Ind.; Stephen R. Fletcher, Buckinghamshire, England

[73] Assignee: The Trustees of Princeton University, Princeton, N.J.

[*] Notice: The portion of the term of this patent subsequent to Aug. 4, 2004 has been disclaimed.

[21] Appl. No.: 220,944

[22] Filed: Jun. 28, 1988

Related U.S. Application Data

[63] Continuation-in-part of Ser. No. 871,539, Jun. 6, 1986, abandoned, which is a continuation-in-part of Ser. No. 835,457, Mar. 3, 1986, Pat. No. 4,684,653, which is a continuation-in-part of Ser. No. 709,622, Mar. 8, 1985, abandoned.

[51] Int. Cl.$^5$ .................. C07D 487/04; A61K 31/505
[52] U.S. Cl. ..................................... 514/258; 544/279; 544/225; 544/226; 546/288; 546/289; 514/184
[58] Field of Search ................ 514/258, 184; 544/279, 544/225, 226

[56] References Cited

U.S. PATENT DOCUMENTS

| | | | |
|---|---|---|---|
| 3,856,959 | 12/1974 | Mead | 424/251 |
| 4,172,200 | 10/1979 | Piper et al. | 544/260 |
| 4,198,415 | 4/1980 | Kornfeld et al. | 546/164 |
| 4,369,319 | 1/1983 | DeGraw et al. | 544/260 |
| 4,380,547 | 4/1983 | Materne | 514/226 |
| 4,431,805 | 2/1985 | Temple et al. | 544/279 |
| 4,432,981 | 2/1984 | Lesher et al. | 424/251 |
| 4,460,591 | 7/1984 | DeGraw et al. | 424/251 |
| 4,512,992 | 4/1985 | Duch et al. | 514/258 |
| 4,526,964 | 7/1985 | Temple et al. | 544/279 |
| 4,532,241 | 7/1985 | DeGraw et al. | 514/258 |
| 4,536,575 | 8/1985 | Temple et al. | 544/279 |
| 4,564,616 | 1/1986 | Jones et al. | 514/260 |
| 4,684,653 | 8/1987 | Taylor et al. | 544/279 |

FOREIGN PATENT DOCUMENTS 1534238 11/1978 United Kingdom .

OTHER PUBLICATIONS

W. L. F. Armarego, "Stereochemistry of Heterocyclic Compounds", Wiley-Interscience, N.Y., (1977), p. 144.
Howard J. Lucas, "Organic Chemistry", 2nd Ed., American Book Company, N.Y., (1953), pp. 313-314.
E. C. Taylor, P. J. Harrington, S. R. Fletcher, G. P. Beardsley, and R. G. Moran, J. Med. Chem., vol. 28 (No. 7), pp. 914-921 (1985).
Moad et al., JACS 101:20, 6068-6076 (9/27/76).
Jahine et al., Ind. J. Chem., 16B, 889-891 (10/78).
Sirotnak et al., Cancer Treat. Rep., 66:2 (21/82).
Troschütz et al., Arch. Pharm. 311, 406-414 (1978).
Temple et al., J. Org. Chem 47, 761-764.
Taylor et al., J. Org. Chem. 50, 1010-1014 (1985).
Taylor et al., Chem. & Biology of Pteridines (Ed. J. A. Blair) 1983, Water de Gruyter & Co., N.Y., 115-119.
Taylor et al., J. Org. Chem. 48, 4852-4860 (1983).
Taylor et al., J. Org. Chem. 50, 1005-1010 (1985).
DeGraw et al., J. Heterocycl. Chem. 19, 1461-1463 1982).
Grivsky et al., J. Med. Chem. 23:3, 327-329 (1980).
Piper et al., J. Med. Chem. 23, 320-321 (1980).
DeGraw et al., J. Med. Chem. 17:5, 552-553 (1974).
Elliott et al., J. Med. Chem. 17:5, 553-555 (1974).
Nair, J. Org. Chem., 50, 1879-1884 (1985).
Drugs of the Future, IV, No. 9, 641-644 (1979).
Sirotnak et al., Cancer Treat. Rep. 62:7, 1047-1052 (1978).
Stone et al., Biochem. Pharmac. 33:2, 175-179 (1984).
Srinivasan et al., J. Org. Chem., 45, 3746-3748 (1980).
Hurlbert et al., J. Med. Chem., 11, 703-707 (1968).
Hurlbert et al., J. Med. Chem., 11, 708-710 (1968).
Hurlbert et al., J. Med. Chem., 11, 711-717 (1968).
Rosowsky et al., J. Med. Chem., 17:12, 1272-1276 (1974).
Struck et al., J. Med. Chem., 14:8, 693-695 (1971).
CA 96:104757a (1982), Sirotnak et al.
Taylor et al., J. Med. Chem. 28:7, 914-921 (1985).
DeGraw et al., J. Heterocycl. Chem. 8, 105-110 (1971).
Oakes et al., J. Chem. Soc. (London), 4433 (1956).
Elslager et al., Lectures in Heterocyclic Chemistry, vol. 2, S-97; Supplement to J. Heterocyclic Chem., 11 (1974).
Horwitz et al., J. Med. Chem. 11:907 (1968).
Harrington, Synthetic Approaches to 5-Deaza and 5,10-Dideaza folic Acid Analogs, Ph.D. Dissertation, Princeton U., 1982.
DeGraw et al., (VII), J. Med. Chem., 17:470 (1974).

(List continued on next page.)

Primary Examiner—Mukund J. Shah
Assistant Examiner—E. Bernhardt
Attorney, Agent, or Firm—Mathews, Woodbridge & Collins

[57] ABSTRACT

The diastereoisomeric forms of N-(4-[2-(2-amino-4-hydroxy-5,6,7,8-tetrahydropyrido[2,3-d]-pyrimidin-6-yl)ethyl]benzoyl)-L-glutamic acid are antineoplastic agents.

The compounds are prepared by separation of the diastereoisomeric form of the correspondingly protected glutamic derivatives and hydrolytic or hydrogenolytic removal of carboxylic acid and/or amino protecting groups.

Typical embodiments are the (R,S) and (S,S) forms of N-(4-[2-(2-amino-4-hydroxy-5,6,7,8-tetrahydropyrido[2,3-d]pyrimidin-6-yl)ethyl]benzoyl)-L-glutamic acid.

13 Claims, No Drawings

OTHER PUBLICATIONS

DeGraw et al., (VIII), J. Heterocyclic Chem., 13:439 (1976).
Smith et al., Biochem. 20: 1241 (1981).
Temple et al., (V), J. Med. Chem. 24: 1254 (1981).
DeGraw et al., (IX), Chem. & Biolog. of Pteridines (Ed. Kisliu Brown) 1979 Elsevier, North Holland (229–234).
Srinivasan et al., (II), J. Org. Chem. 46: 1777 (1981).
Srinivasan et al., (III), Tetrahedron Lett. 23:1431 (1982).
DeGraw et al., (X), PCT Application WO85/02844 (Published Jul. 4, 1985).
Wheeler et al., J. Amer. Chem. Soc. 74:4725 (1952).
Kisliuk, R. L., Nature, 188:584 (1960).
Kisliuk et al., (II), J. Biol. Chem. 239: 1900 (1964).

DIASTEREOISOMERIC TETRAHYDROPYRIDO-(2,3,D) PYRIMIDINE DERIVATIVES

CROSS REFERENCE

This is a continuation-in-part of Ser. No. 871,539, filed June 6, 1986, now abandoned, which in turn is a continuation-in-part of Ser. No. 835,457, filed Mar. 3, 1986, now U.S. Pat. No. 4,684,653, which in turn is a continuation-in-part of Ser. No. 709,622, filed Mar. 8, 1985, now abandoned, the disclosure of each hereby being incorporated by reference herein.

DETAILED DESCRIPTION

This invention pertains to two individual diastereoisomers of N-(4-[2-(5,6,7,8-tetrahydropyrido[2,3-d]pyrimidin-6-yl)alkyl]ethyl]benzoyl)-L-glutamic acid, each substantially free of all other diastereoisomers, to their preparation, and to their use as antineoplastic agent.

The folic acid antimetabolites aminopterin and amethopterin (also known as 10-methylaminopterin or mthotraxate) are antineoplastic agents. These compounds inhibit enzymatic conversions involving metabolic derivatives of folic acid. Amethopterin, for example, inhibits dihydrofolate reductase, an enzyme necessary for the regeneration of tetrahydrofolate from the dihydrofolate which is formed during the conversion of 2-deoxyuridylate to thymidylate by the enzyme thymidylate synthetase.

Other derivatives of folic acid and aminopterin have been synthesized and tested as antimetabolites. Among these are compounds in which a methylene or methylidene group occupies a position in the molecule normally occupied by an imino or nitrilo group, respectively. These derivatives have varying degrees of antimetabolic activity. 10-Deazaaminopterin is highly active (Sirotak et al., Cancer Treat. Rep., 1978, 62, 1047) and 5-deazaminopterin has activity similar to that of amethopterin (Taylor et al., J. Org. Chem., 1983, 48, 4852). 8,10-Dideazaaminopterin is reported to be active (U.S. Pat. No. 4,460,591) and 5,8,10-trideazaaminopterin exhibits activity against mouse L1210 leukemia (Yan et al., J. Heterocycl. Chem., 1979, 16, 541). 10-Deazafolic acid, on the other hand, shows no significant activity (Struck et al., J. Med. Chem., 1971, 14, 693) and 5-deazafolic acid is only weakly cytotoxic. 8,10-Dideazafolic acid is only marginally effective as a dihydrofolate reductase inhibitor (De Graw et al., "Chemistry and Biology of Pteridines", Elsevier, 1979, 229) and 5,8,10-trideazafolic acid also shows only marginal activity against mouse L1210 leukemia (Oatis et al., J. Med. Chem., 1977, 20, 1393). 5,10-Dideazaaminopterin and 5,10-dideaza-5,6,7,8-tetrahydroaminopterin, and the corresponding 5,10-dideazafolic acid derivatives are reported by Taylor et al., J. Med. Chem., 28:7, 914 (1985). The compound N-(4-[2-(2-amino-4-hydroxy-5,6,7,8-tetrahydropyrido[2,3-d]pyrimidin-6-yl)ethyl]benzoyl)-L-glutamic acid has been shown to be a broad spectrum antineoplastic agent.

The compound exists in tautomeric equilibrium with the corresponding 3,4-dihydro-4-oxo compound:

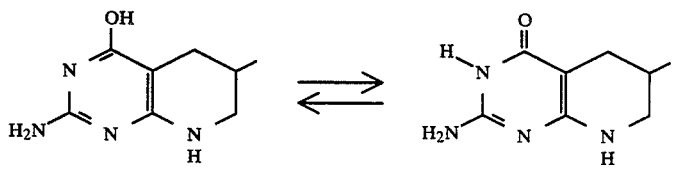

For convenience, the 4-hydroxy form is depicted and the corresponding nomenclature is used throughout this specification, it being understood that in each case such includes the tautomeric 3,4-dihydro-4-keto form.

N-(4-[2-(2-amino-4-hydroxy-5,6,7,8-tetrahydropyrido[2,3-d]YRimidin-6-yl)ethyl]benzoyl)-L-glutamic acid can be prepared according to several routes. In one embodiment, a benzoic acid derivative of the formula:

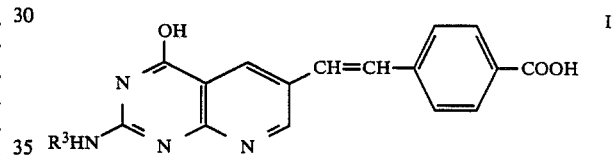

first is coupled with a protected glutamic acid derivative of the formula:

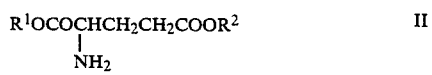

wherein
R¹ and R² are the same or different carboxylic acid protecting group; and
R³ is hydrogen or an amino protecting group.

The amino and carboxylic acid protecting groups are conventional and described for example by Greene in "Protective Groups in Organic Synthesis", John Wiley & Sons, Inc., 1981, and McOmie in "Protective Groups in Organic Chemistry", Plenum Press, 1983.

The coupling reaction also utilizes conventional condensation techniques for forming peptide bonds, such as activation of the carboxylic acid through formation of the mixed anhydride, treatment with DCC, or use of diphenylchlorophosphonate. Thus produced is a compound of the formula:

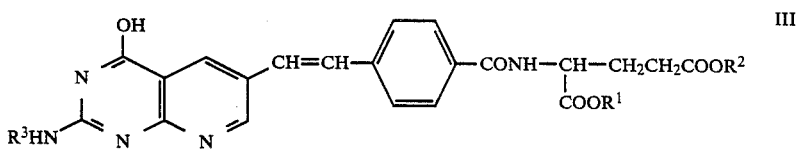

wherein R¹, R² and R³ are as previously defined.

The compound of Formula III then is hydrogenated to yield a protected 5,6,7,8-tetrahydropyrido[2,3-d]pyrimidine of the formula:

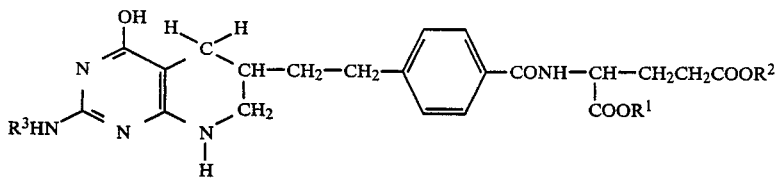

IV wherein R¹, R² and R³ are as previously defined, and hydrolysis or hydrogenolysis to remove the protecting groups then yields the desired N-(4-[2-(2-amino-4-hydroxy-5,6,7,8-tetrahydropyrido[2,3-d]pyrimidin-6-yl)-ethyl]benzoyl)-L-glutamic acid.

Two chiral centers are present in the final molecule: the carbon atom in the 6-position of the tetrahydropyrido[2,3-d]pyrimidine ring and the alpha carbon atom in the glutamic acid group. Of the theoretical four forms of the compound, the use of an L-glutamic acid reagent of Formula II in the initial coupling of the compounds reduces the possibilities to two. Both of these, however, are generated during the subsequent hydrogenation and consequently, upon removal of the protecting groups, the desired compound is produced as a mixture of the (S,S) and (R,S) diastereoisomers:

(S,S):

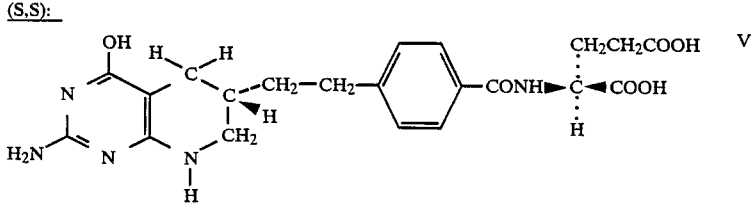

V (R,S):

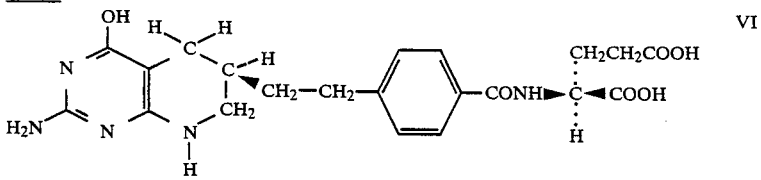

VI

These diastereoisomers can be separated mechanically, as by chromatography, but such is impeded to some degree, particularly in large scale operations, by the low solubility of these compounds in most organic solvents. The mixture of diastereoisomers can be utilized therapeutically, both serving as substrates for relevant folate enzymes. Advantageously, however, since the compounds have somewhat distinct biological profiles, it is desirable to separate each in a form substantially free of the other; i.e., in a form having an optical purity of >95%.

According to the present invention, a solution of a mixture of diastereoisomeric compounds of Formula IV is treated with a chiral acid operable to form a salt therewith. The resultant diastereoisomeric salts are then separated through one or more fractional crystallizations and thereafter the free base of the cationic moiety of at least one of the separated salts is liberated through treatment with a base and removal of the protecting groups. The liberation of the cation of the salt can be performed as a discrete step before or after the removal of the protecting groups, or concomitantly with the removal when such groups are susceptible to removal under basic conditions; i.e., basic hydrolysis.

Suitable chiral acids include the individual enantiomers of 10-camphorsulfonic acid, camphoric acid, alpha bromocamphoric acid, menthoxyacetic acid, tartaric acid, diacetyltartaric acid, malic acid, pyrrolidone-5-carboxylic acid, and the like.

There thus are obtained (i) the diastereoisomer of N-(4-[2(2-amino-4-hydroxy-5,6,7,8-tetrahydropyrido[2,3-d]pyrimidin-6-yl)-ethyl]-benzoyl)-L-glutamic acid having a $[\alpha]_{589\,nm}^{25}$ of $-21.06°$ which is substantially free of the d of N-(4-[2-(2-amino-4-hydroxy-5,6,7,8-tetrahydropyrido[2,3-d]-pyrimidin-6-yl)ethyl]-benzoyl)-L-glutamic acid having a $[\alpha]_{589\,nm}^{25}$ of $+31.09°$ and (ii) the diastereoisomer of N-(4-[2-(2-amino-4-hydorxy-5,6,7,8-tetrahydropyrido-[2,3-d]pyrimidin-6-yl)-ethyl]-benzoyl)-L-glutamic acid having a $[\alpha]_{589\,nm}^{25}$ of $+31.09°$ which in turn is substantially free of the diastereoisomer of N-(4-[2-(2-amino-4-hydroxy-5,6,7,8-tetrahydropyrido[2,3-d]pyrimidin-6-yl)ethyl]-benzoyl)L-glutamic acid having a $[\alpha]_{589\,nm}^{25}$ of $-21.06°$.

The removal of the protecting groups can be acheived through hydrolysis which is conducted at normal temperatures utilizing aqueous acid or base, such as for example, an aqueous alkali metal hydroxide, optionally in the presence of a water miscible organic solvent such as methanol, ethanol, tetrahydrofuran, dimethylformamide, and the like, or an acid, as for example trifluoroacetic acid. When base is used, the cationic moiety of the salt is liberated and the product is formed as the dicationic glutamate salt which can be readily precipitated by adjustment of pH, as through acidification with, for example, acetic acid. The resulting products generally are high melting crystalline or microcrystalline solids.

The individual diastereoisomers of Formulas V and VI, including their pharmaceutically acceptable alkali metal, alkaline earth metal, non-toxic metal, ammonium, and substituted ammonium salts, such as for example the sodium, potassium, lithium, calcium, magnesium, aluminum, zinc, ammonium, trimethylammonium, triethylammonium, triethanolammonium, pyridinium, substituted pyridinium, and the like, have an effect on one or more enzymes which utilize folic acid, and in particular metabolic derivatives of folic acid, as a substrate. The compounds of Formula V and VI can be used, alone or in combination, to treat neoplasms which in the past have been treated with methotrexate, including choriocarcinoma, leukemia, adenocarcinoma of the female breast, epidermid cancers of the head and neck, squamous or small-cell lung cancer, and various lymhosarcomas. The compounds can also be used to treat mycosis fungoides and psoriasis which are responsive to methotrexate.

The compounds may be administered either orally or preferably parenterally, alone or in combination with other anti-neoplastic agents, steroids, etc., to a mammal suffering from neoplasm and in need of treatment. Parenteral routes of administration include intramuscular, intrathecal, intravenous or intraarterial. Dosage regimens must be titrated to the particular neoplasm, the condition of the patient, and the response but generally doses will be from about 10 to about 100 mg/day for 5-10 days or single daily administration of 250-500 mg, repeated periodically; e.g. every 14 days. Oral dosage forms include tablets and capsules containing from 1-10 mg of drug per unit dosage. Isotonic saline solutions containing 20-100 mg/ml can be used for parenteral administration.

The following examples will serve to further illustrate the invention. In the NMR data, "s" denotes singlet, "d" denotes doublet, "t" denotes triplet, "q" denotes quartet, "m" denotes multiplet, and "br" denotes a broad peak.

EXAMPLE 1

[3-Cyano-2-(4-nitrophenylthio)-5-pyridinylmethyl]triphenylphosphonium Bromide

A. A mixture of 60.00 g (0.221 mol) of 3-cyano-2-(4-nitrophenylthio)-5-methylpyridine, 39.37 g (0.221 mol) of N-bromosuccinimide, 3.0 g of benzoyl peroxide and 60 mL of benzene was refluxed for 16 hours while being irradiated with a 275-W sunlamp. The solvent was removed under reduced pressure and the residue was shaken with a mixture of 1 L of water and 1 L of methylene chloride. The organic layer was separated, washed with 1 L of water, dried over anhydrous magnesium sulfate, and filtered. Removal of the solvent by evaporation under reduced pressure yielded 3-cyano-2-(4-nitrophenylthio)-5-bromomethylpyridine which can be used in the following step without further purification.

B. The solid obtained in Part A was stirred at room temperature with a solution of 58.01 g (0.221 mol) of triphenylphosphine in 500 mL of benzene. Filtration of the reaction mixture gave 77.63 g of [3-cyano-2-(4-nitrophenylthio)-5-pyridinylmethyl]triphenylphosphonium bromide.

Stirring of the mother liquor at room temperature for 6 hours afforded an additional 5.67 g, (total yield 83.30 g, 62%). Recrystallization from acetonitrile gave [3-cyano-2-(4-nitrophenylthio)-5-pyridinylmethyl]triphenylphosphonium bromide as light yellow crystals, mp <200° C., with resolidification, mp 253°-256° C. with dec.

C. Alternatively, 3-cyano-2-(4-nitrophenylthio)-5-bromomethylpyridine is allowed to react in tetrahydrofuran with tri-(n-butyl)phosphine for ten hours. Following the addition of ether, the solid which forms is collected by filtration and washed with 1:1 tetrahydrofuran:ether to yield [3-cyano-2-(4-nitro-phenylthio)-pyridin-5-ylmethyl]-tri-(n-butyl)phosphonium bromide as a white solid; mp 175°-176° C.; NMR (CDCl$_3$, 80 MHz) d 0.85-2.63(m, 27H), 4.76(d, 2H, J=15.4 Hz), 7.74(d, 2H, J=9.0 Hz), 8.26(d, 2H, J=9.0 Hz), 8.55 (brs, 1H), 8.79 (brs, 1H); IR (KBr) 2950, 2860, 2220, 1595, 1575, 1515, 1390, 1340, 1075 and 845 cm$^{-1}$; HRMS 471.2116(M$^+$-HBr), Calc'd. for C$_{25}$H$_{34}$N$_3$O$_2$PS471.2109.

EXAMPLE 2

3-Cyano-2-(4-nitrophenylthio)-5-[2-(4-ethoxycarbonylphenyl)ethenyl]pyridine

A. A mixture of 4.544 g (7.42 mmol) of [3-cyano-2-(4-nitrophenylthio)-5-pyridinylmethyl]triphenylphosphonium bromide, 0.751 g (7.42 mmol) of triethylamine and 50 mL of chloroform was stirred at room temperature for 15 minutes and 1.322 g (7.42 mmol) of 4-ethoxycarbonylbenzaldehyde then were added. After stirring at room temperature for 96 hours, 100 mL of water were added, the mixture was filtered, and the organic layer was separated and washed twice with 100 mL portions of water, dried and filtered. Evaporation of the filtrate under reduced pressure gave a residue which was chromatographed on silica gel. Unreacted aldehyde was eluted with 2:1 petroleum ether:benzene, while the title compound was eluted with benzene. Evaporation of the benzene eluate gave 2.82 g (88%) of 3-cyano-2-(4-nitrophenylthio)-5-[2-(4-ethoxycarbonylphenyl)ethenyl]-pyridine as a light yellow solid. The product turns from a solid to a gum below 100° C. and then to a clear liquid between 180° and 220° C.; NMR (Me$_2$SO-d$_6$) delta 1.34 (t, 3H, J=6.3 Hz), 4.32 (q, 2H, J=6.3 Hz), 6.73 (d, 1H, J=13 Hz), 6.99 (d, 1H, J=13 Hz), 7.27 (d, 2H, J=9 Hz), 7.74, 7.85, 7.94 (dd, 2H, 2H), 8.26, 8.31 (dd, 2H, 1H), 8.38 (d, 1H, J=1.8 Hz); IR (KBr) 2220, 1707, 1605, 1597, 1575, 1512, 1344, 1295-1277, 1174 cm$^{-1}$.

Anal.: Calc'd. for C$_{23}$H$_{17}$N$_3$O$_4$S: C, 64.08; H, 3.97; N, 9.74; S, 7.43. Found: C, 63.82; H, 4.01; N, 9.51; S, 7.38.

B. 3-Cyano-2-(4-nitrophenylthio)-5-[2-(4-tertbutoxycarbonylphenyl)ethenyl]pyridine was prepared in 81% yield by the above method utilizing however 4-(tertbutoxycarbonyl)benzaldehyde in place of 4-ethoxycarbonylbenzaldehyde; mp indefinite (cis-trans mixture); NMR (CDCl$_3$) delta 1.62 (s, 9H), 6.43 (d, 1H, J=13 Hz), 6.90 (d, 1H, J=13 Hz), 7.24 (d, 2H, J=9 Hz), 7.69 (d, 2H, J=8.1 Hz), 7.76 (d, 1H, J=2.7 Hz), 7.92 (d, 2H, J=8.1 Hz), 8.22 (d, 2H, J=9 Hz), 8.34 (d, 1H, J=2.7 Hz); IR (KBr) 2220, 1707, 1600, 1577, 1518, 1341, 1290, 1163 cm$^{-1}$.

Anal.: Calc'd for C$_{25}$H$_{21}$N$_3$O$_4$S: C, 65.35; H, 4.61; N, 9.14; S, 6.98. Found: C, 65.28; H, 4,68; N, 9.20; S, 6.93.

EXAMPLE 3

2-Amino-3-cyano-5-[2-(4-ethoxycarbonylphenyl)ethenyl]pyridine

A suspension of 2.00 g (4.64 mmol) of 3-cyano-2-(4-nitrophenylthio)-5-[2-(4-ethoxycarbonylphenyl)-ethenyl]pyridine, 1.553 g (6.95 mmol) of cupric bromide, and 50 mL of liquid ammonia was stirred in a pressure tube at room temperature for 13 days. Evaporation of the ammonia afforded a dark residue which was chromatographed over magnesium silicate using methylene chloride as eluant. The eluate was removed by evaporation under reduced pressure and the residue chromatographed on silica gel. Unreacted starting material was eluted with benzene while 0.87 g (64%) of the product was eluted with ethyl acetate and obtained by evaporation of the ethyl acetate solvent as a light yellow solid, mp 135°–141.5° C.; NMR (Me$_2$SO-d$_6$) delta 1.39 (t, 3H, J=6.3 Hz), 4.38 (q, 2H, J=6.3 Hz), 6.67 (m, 2H), 7.10 (br, 2H), 7.45 (d, 2H, J=9 Hz), 7.71 (d, 1H, J=3.6 Hz), 7.97 (d, 2H, J=9 Hz), 8.11 (d, 1H, J=3.6 Hz); IR (KBr) 3155, 2218, 1715, 1650–1645, 1593, 1491, 1277, 1100 cm$^{-1}$.

Anal. Calc'd. for C$_{17}$H$_{15}$H$_3$O$_2$: C, 69.61; H, 5.16; N, 14.33. Found: C, 69.37; H, 5.25; N, 14.22.

By substituting an equivalent amount of 3-cyano-2-(4-nitrophenylthio)-5-[2-(4-tert-butoxycarbonylphenyl)ethenyl]pyridine in the foregoing procedure there is obtained 2-amino-3-cyano-5-[2-(4-tert-butoxycarbonylphenyl)ethenyl]pyridine; yield 1.14 g (84%) of light yellow crystals, mp 190°–195° C.; NMR (Me$_2$SO-d$_6$) delta 1.57 (s, 9H), 6.57–6.60 (m, 2H), 7.00 (br, 2H), 7.35 (d, 2H, J=8.1 Hz), 7.65 (d, 1H, J=2.7 Hz), 7.84 (d, 2H, J=8.1 Hz), 8.00 (d, 1H, J=2.7 Hz); IR (KBr) 3460, 3360, 2215, 1707, 1623, 1480, 1300, 1287, 1158 cm$^{-1}$.

Anal. Calc'd. for C$_{19}$H$_{19}$N$_3$O$_2$: C, 71.00; H, 5.96; N, 13.07. Found: C, 70.83; H, 6.03; N, 12.83.

EXAMPLE 4

2,4-Diamino-6-[2-(4-tert-butoxycarbonylphenyl)ethenyl]pyrido[2,3-d]pyrimidine.

To a solution of 4.54 mmol of guanidine as the free base (obtained from 0.433 g (4.54 mmol) of guanidine hydrochloride and 0.114 g of sodium in 25 mL of dry tert-butanol) was added 1.325 g (4.12 mmol) of 2-amino-3-cyano-5-[2-(4-tert-butoxyphenyl)ethenyl]pyridine. The deep red suspension was heated at reflux under dry nitrogen for 8 hours. The reaction mixture was cooled to room temperature and filtered. The precipitate was washed successively with water, acetone, and ether and was then dried under reduced pressure to yield 0.911 g (61%) of the title compound as a light yellow solid, mp>350° C., NMR (Me$_2$SO-d$_6$) delta 1.55 (s, 9H), 6.42 (br, 2H), 6.73 (m, 2H), 7.30–8.00 (br, 2H), 7.35 (d, 2H, J=9 Hz), 7.81 (d, 2H, J=9 Hz), 8.34 (m, 2H); IR (KBr) 3320–3300, 3200–3140, 2970, 1718, 1626, 1610–1600, 1550, 1450–1445, 1288, 1167, 812 cm$^{-1}$.

Anal.: Calc'd. for C$_{20}$H$_{21}$N$_5$O$_2$: C, 66.10; H, 5.82; N, 19.27. Found: C, 65.88; H, 5,86; N, 18.98.

EXAMPLE 5

2,4-Diamino-6-[2-(4-carboxyphenyl)ethenyl]pyrido[2,3-d]pyrimidine

A solution of 1.27 g of 2,4-diamino-6-[2-(4-tert-butoxycarbonylphenyl)ethenyl]pyrido[2,3-d]-pyrimidine and 10 mL 88% formic acid were stirred at room temperature. A yellow solid started to form after about 12 hours and after 4 days of stirring, the reaction mixture was filtered. The collected solid was washed well successively with water, methanol, and acetone and was then dried under reduced pressure to give 0.85 g (79%) of the title compound, mp>300° C.

EXAMPLE 6

2-Amino-4-hydroxy-6-[2-(4-carboxyphenyl)ethenyl]pyrido[2,3-d]pyrimidine.

A suspension of 1.0 g of 2,4-diamino-6[2-(4-carboxyphenyl)ethenyl]pyrido[2,3-d]pyrimidine in 30 mL of 1N aqueous sodium hydroxide was heated under reflux under nitrogen for 3 hours. The resulting homogenous orange solution was cooled to room temperature, acidified with 6 mL of glacial acetic acid, and the resulting yellow precipitate collected by filtration. The filter cake was washed successively with water, methanol, acetone and ether and was then dried under reduced pressure to give 0.88 g (88%) of the title compound as a microcrystalline yellow powder, mp>250° C.; NMR (TFA-dl delta 6.8, 7.25 (AB q, 2H, J=12 Hz), 7.45, 8.2 (AB q, 4H, J=9 Hz), 8.55 (s, 1H), 8.85 (s, 1H); IR (Nujol) 3500–2500 (br), 1670, 1625, 1600 cm$^{-1}$.

EXAMPLE 7

Diethyl N-(4-[2-(2-acetamido-4-hydroxypyrido[2,3-d]pyrimidin-6-yl)ethenyl]benzoyl)-L-glutamate A. A suspension of 0.88 g of 2-amino-4-hydroxy-6-[2-(4-carboxyphenyl)ethenyl]pyrido[2,3-d]-pyrimidine in 20 mL of acetic anhydride containing 0.05 g of 4-dimethylaminopyridine was heated under nitrogen at 120° C. for 3 hours. The reaction mixture was cooled to room temperature. Fifty milliliters of ether were added and the resulting yellow solid was collected by filtration to yield 0.95 g (84%) of 2-acetamido-4-hydroxy-6-[2-(4-acetoxycarbonylphenyl)ethenyl]-pyrido[2,3-d]pyrimidine; mp>300° C.; IR (Nujol) 3350, 3150, 1800, 1670, 1600 cm$^{-1}$.

B. To a suspension of 0.95 g of 2-acetamido-4- hydroxy-6-[2-(4-acetoxycarbonylphenyl)ethenyl]-pyrido[2,3-d]pyrimidine in 50 mL of water was added 1N aqueous sodium hydroxide until a homogenous solution was obtained. Acidification with acetic acid resulted in the formation of a yellow precipitate which was collected by filtration. The filter cake was washed sequentially with water, methanol, acetone and ether. The residual solid was recrystallized from DMF to give 0.65 g (77%) of 2-acetamido-4-hydroxy-6-[2-(4-carboxyphenyl)-ethenyl]pyrido[2,3-d]pyrimidine, as a microcrystalline yellow solid, mp>300° C.; NMR (TFA-d ) delta 2.5 (s, 3H), 6.85, 7.32 (AB q, 2H, J=12 Hz), 7.45, 8.18 (AB q, 4H, J=9 Hz), 8.65 (s, 1H), 9.02 (s, 1H); IR (Nujol) 3300–2200 (br), 1685, 1655, 1630, 1600, 1565 cm$^{-1}$. MS: Calc'd. for C$_{18}$H$_{14}$N$_4$O$_4$: 350. Found: m/e 350 (base), 308

C. To an ice cold solution of 1.5 g (0.0043 mol) of 2-acetamido-4-hydroxy-6-[2-(4-carboxyphenyl)-ethenyl]pyrido[2,3-d]pyrimidine in 40 mL of N-methylpyrrolidone containing 1.4 mL of N-methylmorpholine was added 1.72 g (0.0064 mol) of phenyl N-phenylphosphoramidochloridate in a single portion. The resulting mixture was stirred at 0° C. for 30 minutes. Diethyl L-glutamate hydrochloride (1.53 g, 0.0064 mol) was then added and the reaction mixture was stirred at room temperature overnight. The solvent was evaporated under reduced pressure and the residual solid triturated with 50 mL of 1N aqueous sodium carbonate. The mixture was filtered and the collected solid dissolved in 20 mL of chloroform. The chloroform solution was dried over anhydrous magnesium sulfate and filtered. The filtrate was evaporated to dryness and chromatographed on silica gel. Elution with chloroform:methanol (95:5) gave 1.52 g (66%) of diethyl N-(4-[2-(2-acetamido-4-hydroxypyrido[2,3-d]pyrimidin-6-yl)ethenyl]benzoyl)-L-glutamate mp>250° C.; NMR (CDCl$_3$Me$_2$SO-d$_6$) delta 1.15-1.45 (2t, 6H, J=6 Hz), 2.0-2.65 (m, 4H), 2.3 (s, 3H), 4.0-4.35 (2q, 4H, J=6 Hz), 4.5-4.75 (m, 1H), 6.7, 6.9 (AB q, 2H, J=15 Hz), 7.33, 7.84 (AB q, 4H, J=9 Hz), 8.25-8.38 (m, 2H), 8.62 (d, 1H, J=2Hz), 11.5-12.5 (br, 2H); IR (Nujol) 3320, 3150, 1730, 1680, 1630, 1600 cm$^{-1}$.

Anal.: Calc'd. for C$_{27}$H$_{29}$N$_5$O$_7$: C, 60.56; H, 5.42; N, 13.08. Found: C, 60.26; H, 5.45; N, 12.84.

EXAMPLE 8

Diethyl N-(4-[2-(2-acetamido-4-hydroxy-5,6,7,8-tetrahydropyrido[2,3-d]pyrimidin-6-yl)ethyl]-benzoyl)-L-glutamate A solution of diethyl N-(4-[2-(2-acetamido-4-hydroxypyrido[2,3-d]pyrimidin-6-yl)ethenyl]benzoyl-L-glutamate in 30 mL of trifluoroacetic acid was hydrogenated at 55 psi of hydrogen in the presence of 1.0 g of 5% Pd/C at room temperature for 14 hours. The catalyst was removed by filtration, the filtrate evaporated under reduced pressure, and the residual solid partitioned between 100 mL of chloroform and 50 ml of 2N aqueous sodium carbonate. The organic phase was separated, dried over anhydrous magnesium sulfate, and the solvent removed by evaporation to give a gum which was chromatographed on silica gel. Elution with chloroform:methanol (97:3) gave 0.25 g (56%) of diethyl N-(4-[2-(2-acetamido-4-hydroxypyrido[2,3-d]pyrimidin-6-yl)ethyl]benzoyl)-L-glutamate; mp 215°-217° C.; NMR (CDCl$_3$) delta 1.25, 1.35 (2t, 6H, J=6 Hz), 2.1-2.5 (m, 4H), 2,55 (s, 3H), 3.1 (s, 4H), 4.15, 4.25 (2q, 4H, J=6 Hz), 4.6-4.96(m, 1H), 7.05 (s, 1H), 7.25, 7.75(AB q, 4H, J=9 Hz), 8.35 (d, 1H, J=3 Hz), 8.77 (d, 1H, J=3 Hz); IR (Nujol) 3200, 3150, 1725, 1675, 1630, 1605 cm$^{-1}$.

Anal.: Calc'd. for C$_{27}$H$_{31}$N$_5$O$_7$: C, 60.32; H, 5.81; N, 13.03. Found: C, 59.98; H, 6.03; N, 12.92).

Further elution with 95:5 chloroform:methanol yielded 0.08 g (18%) of the title compound, mp>200° C.; NMR (CDCl$_3$/Me$_2$SO-d$_6$) delta 1.24, 1.28 (2t, 6H, J=6 Hz), 1.5-3.3 (m, 13H), 2.18 (s, 3H), 4.1, 4.18 (2a, 4H, J=6 Hz), 4.4-4.7 (m,1H), 6.2 (s, 1H), 7.28, 7.85 (AB q, 4H, J=9 Hz), 8.4 (d, 1H, J=8 Hz); IR (Nujol) 3320, 3250, 1730, 1630, 1575 cm$^{-1}$. Anal.: Calc'd. for C$_{27}$H$_{35}$N$_5$O$_7$: C, 59.87; H, 6.51; N, 12.93. Found: C, 59.66; H, 6.71; N, 12.77.

EXAMPLE 9

A mixture of 1.0 g of diethyl N-(4-[2-(2-acetamido-4-hydroxy-5,6,7,8-tetrahydropyrido[2,3-d]-pyrimidin-6-yl)ethyl]benzoyl)-L-glutamate and 880 mg of d(+)-10-camphorsulfonic acid in 50 mL of anhydrous ethanol is heated at reflux for 4 hours. The reaction mixture was allowed to cool to room temperature and to stand overnight. The white solid which formed was collected by filtration and fractionally crystallized six times in ethanol to yield 37 mg of diastereoisomer "B" of diethyl N-(4-[2-(2-acetamido-4-hydroxy-5,6,7,8-tetrahydropyrido[2,3-d]pyrimidin-6-yl)ethyl]benzoyl)-L-glutamate d(+)-10-camphorsulfonate, m.p. 223°-225° C., [α]$_{589\ nm}^{25}$=20.02°.

The solvent is removed from the mother liquor by evaporation and the solid which forms is recrystallized twice from ethanol to yield diastereoisomer "A" of diethyl N-(4-[2-(2-acetamido-4-hydroxy-5,6,7,8-tetrahydropyrido[2,3-d]pyrimidin-6-yl)ethyl]benzoyl)-L-glutamate d(+)-10-camphorsulfonate, [α]$_{589\ nm}^{25}$=+29.35°.

EXAMPLE 10

Diastereoisomer "B" of N-(4-[2-(2-amino-4-hydroxy-5,6,7,8-tetrahydropyrido[2,3-d]pyrimidin-6-yl)ethyl]benzoyl)-L-glutamic acid A solution of diastereoisomer "B" of diethyl N-(4-[2-(2-acetamido-4-hydroxy-5,6,7,8-tetrahydropyrido[2,3-d]pyrimidin-6-yl)ethyl]benzoyl)-L-glutamate d(+)-10-camphorsulfonate in 50 mL of methanol containing 3 mL of 1N aqueous sodium hydroxide was stirred at room temperature for 72 hours. Addition of 2 mL of acetic acid followed by centrifugation yielded diastereoisomer "B" of N-(4-[2-(2-amino-4-hydroxy-5,6,7,8-tetrahydropyrido[2,3-d]pyrimidin-6-yl)ethyl]benzoyl)-L-glutamic acid, mp 224°-227° C. (dec.) [α]$_{589\ nm}^{25}$=21.0581° (c=0.636, 0.1N NaOH); λ$_{max}$ 278 nm, 222 nm; NMR (CDCl$_3$) delta 1.85 (m, 2H), 1.98 (m, 1H), 2.25 (m, 1H), 2.45 (m, 1H), 2.68 (m 1H), 2.92 (m, 5H), 3.25 (t, J=10 Hz, 1H), 3.82 (d, J =10Hz, 1H), 513 (m, 1H) 7.43 (d, J=9 Hz, 2H), 7.84 (d, J =9 Hz, 2H). The optical purity is >97%. Ten grams of diastereoisomer "B" of N-(4-[2(2-amino-4-hydroxy-5,6,7,8-tetrahydropyrido[2,3-d]pyrimidin-6-yl)ethyl]benzoyl)-L-glutamic acid were suspended in 40 mL of water (pH about 5.0). To this suspension was added dropwise with stirring, 8 mL of 5.0N aqueous sodium hydroxide and then 1.0N aqueous sodium hydroxide until all the solid was in solution (about 3.5 mL). The pH of the solution was about 8. Fifty milliliters of methanol then were added and the solution allowed to stand in the refrigerator overnight. The solid which formed was collected by filtration, washed with a small amount of cold methanol, and dried under vacuum at room temperature to yield the disodium salt diastereoisomer "B" of N-(4-[2-(2-amino-4-hydroxy-5,6,7,8-tetrahydropyrido[2,3-d]pyrimidin-6-yl)ethyl]benzoyl)-L-glutamic acid (8.1 g). IR (KBr)=3440-3120, 1640, 1620, 1600, 1548, 1504, 1402, 1368, 1310 cm$^{-1}$; NMR (300 MHz, D$_2$O), delta 7.76 (d, 2H, J=6 Hz), 4.32 (q, 1H, J=9 Hz, J=5 Hz), 3.33 (q, 1H, J=11 Hz, 2 Hz), 2.95 (q, 1H, J=11, 9 Hz), 2.75 (m, 2H, 2.55 (q, 1H, J=11 Hz, 3 Hz), 1.20 (t, 2 H, J=7 Hz), 2.17 (m, 1H), 2.14 (m, 2 Hz), 1.76 (m, 1H), 1.68 (m, 3H).

Anal. Calc'd. for C$_{21}$H$_{29}$N$_5$O$_9$Na$_2$: C, 46.58; H, 5.40; N, 12.93. Found: C, 45.98; H, 5.20; N, 12.40.

EXAMPLE 11

Diastereoisomer "A" of N-(4-[2-(2-amino-4-hydroxy-5,6,7,8-tetrahydropyrido[2,3-d]pyrimidin-6-yl)-ethyl]benzoyl)-L-glutamic acid By following the procedure of Example 10, but utilizing diastereoisomer "A" of diethyl N-(4-[2-(2-acetamido-4-hydroxy-5,6,7,8-tetrahydropyrido[2,3-d]-pyrimidin-6-yl)ethyl]benzoyl)-L-glutamate d(+)-10-camphorsulfonate in place of diastereoisomer "B", there is obtained diastereoisomer "A" of N-(4-[2-(2-amino-4-hydroxy-5,6,7,8-tetrahydropyrido[2,3-d]pyrimidin-6-yl)ethyl]benzoyl)-L-glutamic acid, mp 253°-255° C. (dec.) [α]$_{589\ nm}^{25}$=+31.0915° (c=3.605, 0.1N NaOH); λ$_{max}$ 278 nm, 222 nm; NMR (CDCl$_3$) delta 1.85 (m, 2H), 1.98 (m, 1H), 2.25 (m, 1H), 2.45 (m, 1H), 2.68 (m 1H), 2.92 (m, 5H), 3.25 (t, J=10 Hz, 1H), 3.82 (d, J=10 Hz, 1H), 513 (m, 1H) 7.43 (d, J=9 Hz, 2H), 7.84 (d, J=9 Hz, 2H). The optical purity is >97%.

EXAMPLE 12

The $IC_{50}$ value was determined in whole cell human leukemia cell lines, CCRF-CEM, for diastereoisomer "A" of Example 11 and diastereoisomer "B" of Example 10. Results of these experiments are as follows:

| Compound | $IC_{50}$ (mcg/mL) |
|---|---|
| Diastereoisomer "A" | $2.6 \times 10^{-3}$ |
| Diastereoisomer "B" | $3.4 \times 10^{-3}$ |

EXAMPLE 13

B-16 melanoma tumor cells were implanted subcutaneously in the axillary region of C57BL/G mice. Groups of ten mice were used for each dosage. Following daily intraperitoneal administration of diastereoisomer "B" of N-(4-[2-(2-amino-4-hydroxy-5,6,7,8-tetrahydropyrido[2,3-d]pyrimidin-6-yl)ethyl]benzoyl)-L-glutamic acid, the length and width of the control tumor (receiving only saline) was measured after ten days and compared to those of animals receiving the test compound to calculate percentage of inhibition. The results are as follows:

| Dose (mg/kg) | % Inhibition | Survivors |
|---|---|---|
| 1.60 | 71 | 10/10 |
| 3.12 | 91 | 10/10 |
| 6.25 | 98 | 10/10 |
| 12.50 | 100 | 10/10 |
| 25.00 | 100 | 10/10 |
| 50.00 | 100 | 9/10 |
| 100.00 | 100 | 8/10 |
| 200.00 | 100 | 6/10 |

The administration of diastereoisomer "A" at dosages of 1.60 and 3.12 mg/kg resulted in 47% and 24% inhibition, respectively, of B-16 melanoma in the above procedure. The compound was ineffective against this tumor line at higher doses.

What is claimed is:

1. A compound selected from the group consisting of:
   (i) the diastereoisomer of N-(4-[2-(2-amino-4-hydroxy-5,6,7,8-tetrahydropyrido[2,3-d]-pyrimidin-6-yl)ethyl]-benzoyl)-L-glutamic acid having a $[\alpha]_{589\ nm}^{25}$ of $-21.06°$ and being substantially free of the isomer of N-(4-[2-(2-amino-4-hydroxy-5,6,7,8-tetrahydropyrido[2,3-d]pyrimidin-6-yl)ethyl]-benzoyl)-L-glutamic acid which has a $[\alpha]_{589\ nm}^{25}$ of $+31.09°$;
   (ii) the 4(3H)-ox form thereof; and
   (iii) a pharmaceutically acceptable alkali metal, alkaline earth, non-toxic metal, ammonium, or substituted ammonium salt thereof which is substantially free of the corresponding salt of that diastereoisomer which has a $[\alpha]_{589\ nm}^{25}$ of $+31.09°$.

2. The diastereoisomer of N-(4-[2-(2-amino-4-hydroxy-5,6,7,8-tetrahydropyrido[2,3-d]pyrimidin-6-yl)-ethyl]-benzoyl)-L-glutamic acid having a $[\alpha]_{589\ nm}^{25}$ of $-21.06°$ and being substantially free of isomer of N-(4-[2-(2-amino-4-hydroxy-5,6,7,8-tetrahydropyrido[2,3-d]pyrimidin-6-yl)ethyl]benzoyl)-L-glutamic acid which has a $[\alpha]_{589\ nm}^{25}$ of $+31.09°$.

3. The method of combating neoplastic growth in a mammal which comprises administering to the mammal in a single or multiple dose regimen an effective amount of a compound according to claim 1.

4. The method of combating neoplastic growth in a mammal which comprises administering to the mammal in a single or multiple dose regimen an effective amount of a compound according to claim 2.

5. A pharmaceutical composition for combating neoplastic growth in a mammal which comprises an amount of a compound according to claim 1 which upon administration to the mammal in a single or multiple dose regimen is effective to combat said growth, in combination with a pharmaceutically acceptable carrier.

6. A pharmaceutical composition for combating neoplastic growth in a mammal which comprises an amount of a compound according to claim 2 which upon administration to the mammal in a single or multiple dose regimen is effective to combat said growth, in combination with a pharmaceutically acceptable carrier.

7. A compound selected from the group consisting of:
   (i) the diastereoisomer of N-(4-[2-(2-amino-4-hydroxy-5,6,7,8-tetrahydropyrido[2,3-d]-pyrimidin-6-yl)ethyl]-benzoyl)-L-glutamic acid having a $[\alpha]_{589\ nm}^{25}$ of $+31.09°$ and being substantially free of the isomer of N-(4-[2-(2-amino-4-hydroxy-5,6,7,8tetrahydropyrido[2,3-d]pyrimidin-6-yl)ethyl]-benzoyl)-L-glutamic acid which has a $[\alpha]_{589\ nm}^{25}$ of $-21.06°$;
   (ii) the 4(3H)-oxo form thereof; and
   (iii) a pharmaceutically acceptable alkali metal, alkaline earth, non-toxic metal, ammonium, or substituted ammonium salt thereof which is substantially free of the corresponding salt of that diastereoisomer which has a $[\alpha]_{589\ nm}^{25}$ of $-21.06°$.

8. The disodium salt of the diastereoisomer according to claim 7.

9. The diastereoisomer of N-(4-[2-(2-amino-4-hydroxy-5,6,7,8-tetrahydropyrido[2,3-d]pyrimidin-6-yl)ethyl]-benzoyl)-L-glutamic acid having a $[\alpha]_{589\ nm}^{25}$ of $+31.09°$ and being substantially free of the diastereoisomer of N-(4-[2-(2-amino-4-hydroxy-5,6,7,8-tetrahydropyrido[2,3-d]pyrimidin-6-yl)ethyl]benzoyl)-L-glutamic acid which has a $[\alpha]_{589\ nm}^{25}$ of $-21.06°$.

10. The method of combating neoplastic growth in a mammal which comprises administering to the mammal in a single or multiple dose regimen an effective amount of a compound according to claim 7.

11. The method of combating neoplastic growth in a mammal which comprises administering to the mammal in a single or multiple dose regimen an effective amount of a compound according to claim 9.

12. A pharmaceutical composition for combating neoplastic growth in a mammal which comprises an amount of a compound according to claim 7 which upon administration to the mammal in a single or multiple dose regimen is effective to combat said growth, in combination with a pharmaceutically acceptable carrier.

13. A pharmaceutical composition for combating neoplastic growth in a mammal which comprises an amount of a compound according to claim 9 which upon administration to the mammal in a single or multiple dose regimen is effective to combat said growth, in combination with a pharmaceutically acceptable carrier.

* * * * *